United States Patent [19]

Yamada

[11] 4,072,822
[45] Feb. 7, 1978

[54] TWO-WAY STETHOSCOPE FOR DIRECT AND AMPLIFIED SOUND

[76] Inventor: Yoshihito Yamada, 2-9, Imagawa 4-chome, Suginami-ku, Tokyo, Japan

[21] Appl. No.: 727,087

[22] Filed: Sept. 27, 1976

[51] Int. Cl.² .............................................. A61B 7/04
[52] U.S. Cl. ............................. 179/1.5 T; 128/2.05 S
[58] Field of Search ................ 179/1.5 T; 128/2.05 S, 128/2 K

[56] References Cited

U.S. PATENT DOCUMENTS

| 3,160,708 | 12/1964 | Andries | 179/1.5 T |
| 3,247,324 | 4/1966 | Cefaly | 179/1.5 T |

*Primary Examiner*—William C. Cooper
*Assistant Examiner*—Kenneth A. Chayt
*Attorney, Agent, or Firm*—William Anthony Drucker

[57] ABSTRACT

The present invention relates to a stethoscope, more particularly to a two-way stethoscope which permits hearing both direct and amplified sound from the human body through manipulation of a simple switching means at hand. The microphone for the electronic mode is located in the chestpiece, while the earpieces contain the speakers.

3 Claims, 12 Drawing Figures

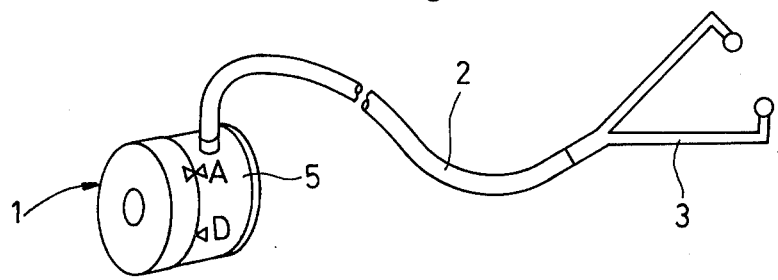
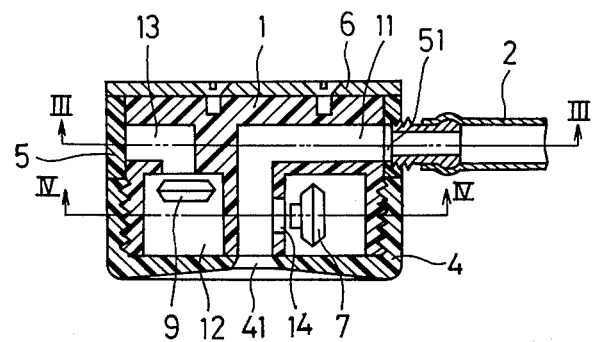
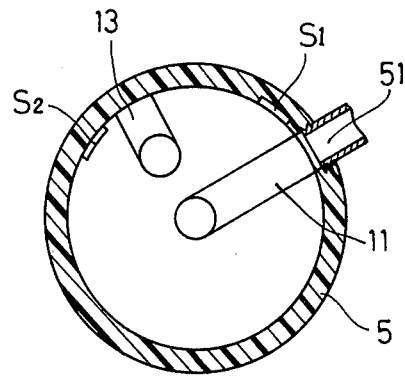
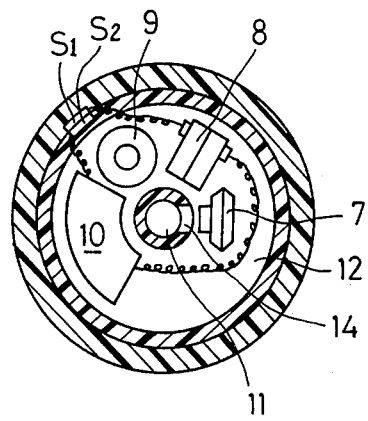

TWO-WAY STETHOSCOPE FOR DIRECT AND AMPLIFIED SOUND

BACKGROUND OF THE INVENTION

The invention relates to a two-way stethoscope which permits hearing either direct or amplified sound from the human body.

As stethoscopes used by physicians in examining patients, there are of late, besides usual well-known tubular ones, amplifying stethoscopes which electrically magnify sound. The latter, however, may not clearly transmit sound from a body in places with much electrical noise, for example, in vicinity of a running high frequency sewing machine. Further, necessity may occur to hear the live unamplified sound by reason of diagnostic techniques. The inconvenience with the conventional stethoscopes is that one must prepare the two types of stethoscopes, a usual tubular one and an amplifying one, and changes them in every necessary case.

SUMMARY OF THE INVENTION

The primary object of the invention is to provide a two-way stethoscope which, through simple manipulation of a switch at hand, functions either as a tubular stethoscope or as an amplifying one, and thereby to eliminate the above-mentioned inconvenience.

Another object of the invention is to provide a two-way stethoscope which has a simple construction and is of easy switching operation.

BRIEF DESCRIPTION OF DRAWINGS

In the accompanying drawings

FIG. 1 is an oblique view generally showing an embodiment of the invention;

FIG. 2 is a side elevational view of a section of an embodiment of the contactor;

FIGS. 3 and 4 are cross sections taken along Lines III—III and IV—IV in FIG. 2 respectively;

DETAILED DESCRIPTION OF THE INVENTION

Figure 5:
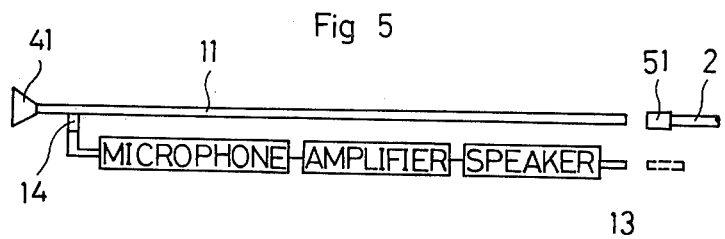
FIG. 5 is a diagram of transmission routes of sound.

In FIG. 1 or FIG. 2, numeral 1 designates the body of a contactor which is connected through a sound tube 2 to an ear tube 3 for either single or both ears (shown in FIG. 1 is a tube for both ears).

The contactor body 1 is of circular cylindrical shape and has a passage 11 which first extends along the axis of the body and, turning to the radial direction, reaches the peripheral wall, a recess 12 coaxial with said passage, and another passage 13 which extends from said recess 12 and ends in the peripheral wall. The passage 11 and the recess 12 are communicated with each other through a passage 14.

A cover 4 is attached over the recess 12 after electronic amplifying means to be described hereinafter are accommodated therein. The cover 4 is provided at its center with sound pickup hole 41 fitting with the passage 11, and is mounted to the contactor body by means of a threaded case, which will be a convenient feature when the electronic devices are inspected.

With the outer periphery of the contactor body 1 coaxially engages a circular turn ring 5, which is provided in the periphery thereof with a hole 51 congruent with each of the end openings of the passages 11 and 13, and said sound tube 2 is connected to said hole 51. $S_1$ and $S_2$ are switch terminals set in the periphery of the turn ring and the body 1, respectively. The switch consisting of these terminals is closed when said hole 51 is adjusted to said passage 13 and thereby energizes the amplifier to be described hereinafter. Numeral 6 designates a rear cap which prevents the rotable ring 5 from falling off.

FIG. 4 shows schematically the generating means of amplified sound which comprises a microphone means 7 provided to face the end opening of the passage 14, a very small-size electric source 8 such, for example, as a mercury cell, a speaker means 9 provided to face the end of the passage 13 and an amplifier 10. In these electronic means, integrated circuits may be employed if further miniaturization is necessary. The principles and means of sound amplification are well known and further description thereof may be omitted. As the electric supply, an exterior power source of greater capacity may be used.

The use of a stethoscope according to the invention is as follows. First, in order to use as a usual tubular stethoscope to hear direct sound, the hole 51 of the turn ring 5 is adjusted to the end opening of the passage 11 as shown in FIG. 2. This state corresponds to the upper route of FIG. 5. Then, if electrically amplified sound is wanted, the hole 51 is adjusted to the end opening of the passage 13, and switch terminals $S_1$ and $S_2$ come in contact with each other as shown in FIG. 4 thereby energizing the amplifying means. This state corresponds to the lower route of FIG. 5. In either case, the marks D (Direct) or A (Amplified) on the turn ring adjusted to the reference mark clearly indicate the state of the stethoscope.

Now another embodiment of the invention shall be described.

Figure 6:
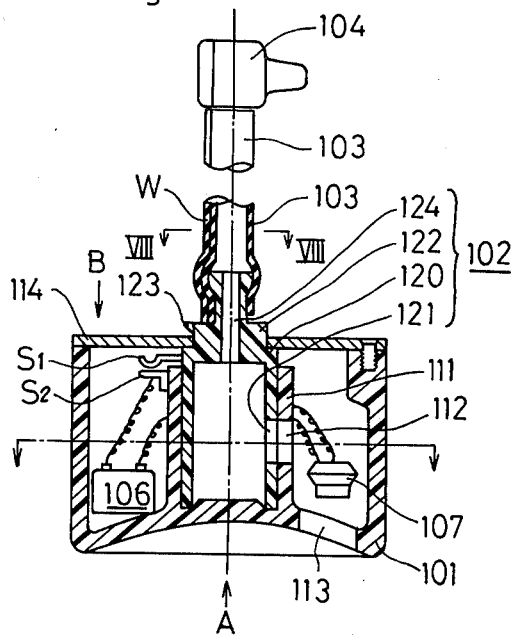
FIG. 6 is a side elevational sectional view showing another embodiment of the invention.
Figure 8:
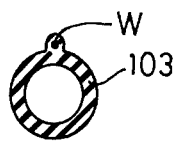
FIG. 8 is a similar view taken along Line VIII—VIII of FIG. 6.
Figure 7:
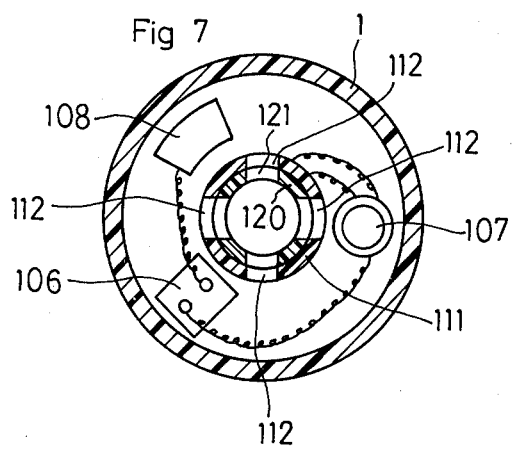
FIG. 7 is a section taken along Line VII—VII of FIG. 6.
Figure 9:
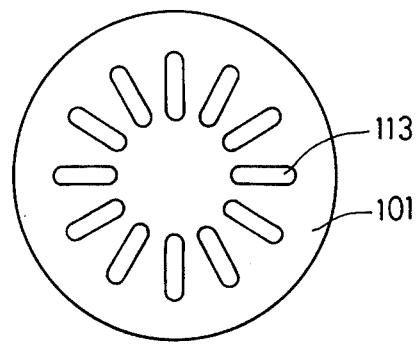
FIG. 9 is a view seen in the direction of the arrow A of FIG. 6.

Referring to FIG. 6, 101 designates a contactor body which makes generally a hollow circular cylinder, of which one end is closed. In the inner peripheral wall 111 which is formed to be coaxial with, and inside of, the outer peripheral wall are provided communication holes 112 at regular intervals (four holes in this embodiment). In the end surface of the contactor body 101 are provided a plurality of sound pickup holes 113 which communicate with the space defined by the outer and inner walls as clearly shown in FIG. 9.

Figure 10:
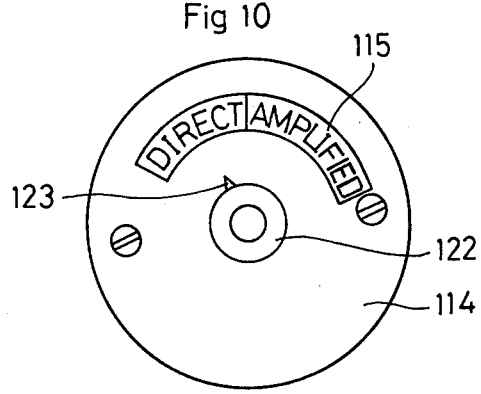
FIG. 10 is a view seen in the direction of the arrow B of the same FIG. 6.

A switching turn tube 102 is provided inside the inner periphery to engage rotatably therewith. The turn tube 102 is formed to be a generally hollow circular cylinder having a through hole 124. In the periphery 120 thereof are formed communication holes 121 corresponding to said hole 112, and at the stepped portion 122 of lesser diameter is provided an arrow mark 123. Further, in a portion of the periphery 120 is attached a switch terminal $S_1$ which, through contact with another switch terminal $S_2$ provided in the inner periphery 111, energizes the amplifying means to be described hereinafter. A cover 114 is attached to the contactor body after the turn tube 102 is set therein to prevent falling off thereof. On the cover 114 is, as shown in FIG. 10, provided a divided band mark 115 to which the arrow 123 is to point to indicate which mode, direct or amplified, is enabled.

Within the space between the inner and outer peripheries are arranged a small-sized electric source 106 such as a mercury cell, a microphone means 107 for transforming the sound picked up through said pickup holes into electric signals, and an amplifying means 108 for amplifying said electric signals, made as small as possible by employing, for example, an integrated circuit.

Figure 11:
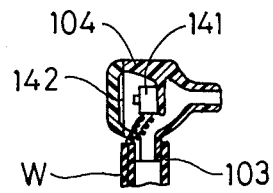
FIG. 11 is a vertical section of the earphone.
Figure 12:
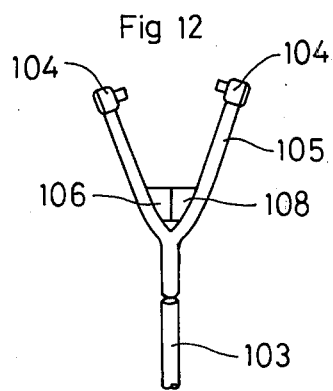
FIG. 12 is a plan view showing another arrangement of the electric source and the amplifier.

On one end of the switching turn tube 102 is fitted a hollow sound tube 103 to communicate with the hollow space thereof. In a portion of the sound tube 103 is buried an electric wire W which transmits the varying electric current sent out from the amplifier 108 to the electromagnet 141 of an earphone 104 provided at the other end of the sound tube 103 (FIG. 11). In FIG. 11, 142 is a diaphragm.

The use of this embodiment is almost the same with that of the previous embodiment. To describe briefly, when direct sound is to be heard, the communication hole 121 formed in the periphery 120 of the switching turn tube 102 is adjusted to the communication hole 112 of the contactor body 1 as shown in FIG. 6, thereby transmitting the sound from the sound pickup hole 113 through the hole 124 and the sound tube 103 to the earphones 104. The inside of the earphones 104 is hollow and includes nothing but a support for the electromagnet 141, which will not hinder the transmission of the sound. In this case the switch terminals $S_1$ and $S_2$ are in positions not to contact each other.

When amplified sound is desired, it suffices to turn the switching tube 102 and adjust the arrow 123 to the "Amplify" mark of the band mark 115. In this case, the communication between the holes 112 and 121 is cut off and conversely the switch terminals $S_1$ and $S_2$ are brought into contact with each other to energize the amplifier circuit, the sound from the sound pickup hole 113 thereby being converted through the microphone means 107 and the amplifier 108 into varying current which in turn is received by the electromagnet 141 actuating diaphragm 142 of the earphone 104 and transformed into amplified sound.

As in a modified embodiment (not shown in the drawings) of the invention, the electric source 106 and the amplifier 108 may be set in the Y tube 105 which has at the end thereof earphones 108. This arrangement will effectuate reduction in size of the contactor body 101.

As apparently seen from the detailed descriptions hereinabove, this invention is practically very effective and useful in that it makes it possible to hear either direct or amplified sound through a slight turn of the switching tube and in that the stethoscope will be very compact due to the employment of a cavity type earphone and a small-sized transmitter.

The invention, as will be clearly understood by those skilled in the art from the detailed description hereinabove, will contribute to improvement of diagnostic techniques by making it possible to hear direct and amplified sound separately through a simple operation of a switching means at hand, and has many effects such, to mention a few, that only a single sound tube is needed which simplifies the external appearance of the stethoscope, that the inconvenience of preparing and carrying another cord can be avoided, and that the construction is generally simple and seldom liable to troubles.

What is claimed is:

1. A two-way stethoscope, for use selectively with direct and amplified transmission of sound comprising:
   (i) a hollow generally cylindrical contactor body having an end wall with a plurality of sound pickup holes therein, and having an inner cylindrical wall with a plurality of communication holes therein;
   (ii) a hollow cylindrical turn tube having a plurality of communiction holes therein, said turn tube being engaged within said inner cylindrical wall of said contactor body;
   (iii) a sound tube having two ends, said tube being connected at one end to said turn tube and communicating with the interior thereof;
   (iv) at least one earphone provided at the other end of said sound tube, said earphone being hollow and including an electromagnet and a diaphragm;
   (v) a microphone means, for transforming sound entering through said pickup holes into electric signals, arranged in the hollow space of said contactor body;
   (vi) an amplifying means connected to said microphone means;
   (vii) an electric current source for said amplifying means;
   (viii) a conducting lead integral with said sound tube, said lead connecting at one end to said amplifying means and at the other end to said earphone, and
   (ix) a switching means for interrupting the current flow between said current source and said amplifying means, said switching means consisting of a first switch contact mounted on said turn tube and a second switch contact mounted on said contactor body, said first and second contacts being positioned so as not to be in contact with each other when the turn tube is in a position of rotation with respect to the contactor body in which the communication holes of the turn tube coincide with the communication holes of the contactor body, said contacts being adapted to contact each other in another position of relative rotation in which the respective communication holes do not coincide.

2. A two-way stethoscope, according to claim 1, wherein said electric current source and said amplifying means are positioned in said contactor body.

3. A two-way stethoscope, according to claim 1, wherein said electric current source and said amplifying means are provided on said sound tube.

* * * * *